United States Patent [19]

Kawasaki et al.

[11] Patent Number: 5,023,898
[45] Date of Patent: Jun. 11, 1991

[54] X-RAY RADIOGRAPHIC SYSTEM

[75] Inventors: Mikio Kawasaki; Masatoshi Iwata, both of Hino, Japan

[73] Assignee: Konica Corporation, Tokyo, Japan

[21] Appl. No.: 470,979

[22] Filed: Jan. 26, 1990

[30] Foreign Application Priority Data

Feb. 2, 1989 [JP] Japan .................................. 1-24964

[51] Int. Cl.⁵ ............................................. G21K 5/10
[52] U.S. Cl. ..................................... 378/146; 378/145
[58] Field of Search ................................ 378/145, 146

[56] References Cited

U.S. PATENT DOCUMENTS 4,715,056 12/1987 Vlasbloem et al. ................. 378/146
4,803,714 2/1989 Vlasbloem .......................... 378/146

FOREIGN PATENT DOCUMENTS 147854 7/1985 European Pat. Off. .
223432 5/1987 European Pat. Off. .
2114309 8/1983 United Kingdom .

OTHER PUBLICATIONS

Patent Abstracts of Japan; vol. 12, No. 163 (P-703)[3010]; 5/18/86, JPA-62-276539, 12/1/87.

Primary Examiner—Craig E. Church
Attorney, Agent, or Firm—Jordan B. Bierman

[57] ABSTRACT

An X-ray radiography system comprising divided fan beam scanning device, feed-back the beam regulator and a silver halide photosensitive material having a covering power not less than 45 which is capable to diagnose wide range of photodensity area at one time exposure for minimizing the radiation dose is disclosed.

11 Claims, 2 Drawing Sheets

FIG. I
(a)
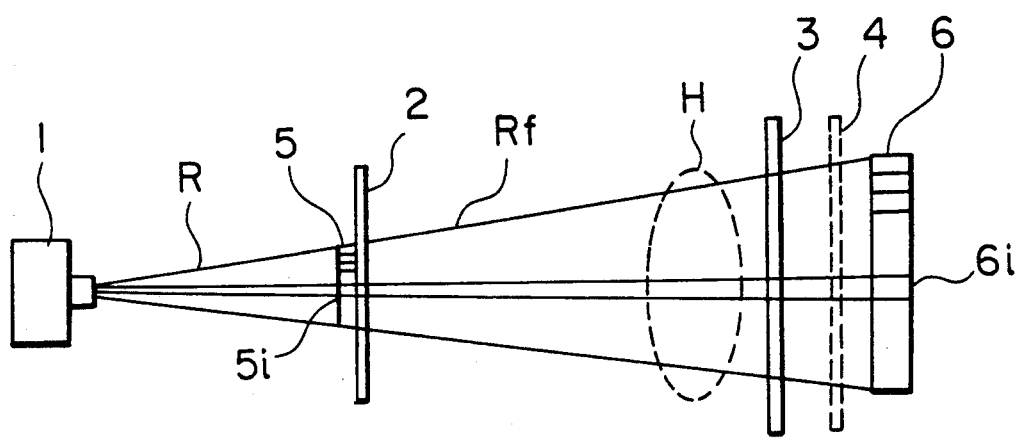
(b)
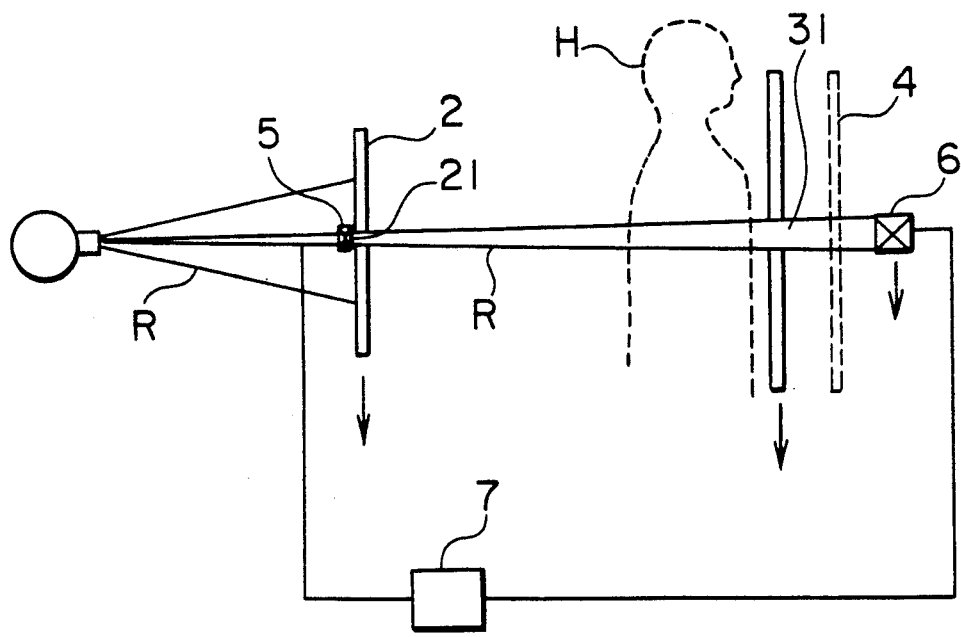

X-RAY RADIOGRAPHIC SYSTEM

FIELD OF THE INVENTION

This invention relates to an X-ray diagnostic system using a silver halide light-sensitive material.

BACKGROUND OF THE INVENTION

Generally, in X-ray photographic silver halide light-sensitive materials applicable to medical diagnoses or the like (hereinafter referred to as X-ray light-sensitive materials), a high-speed emulsion containing silver halide grains having a large size of several microns are coated on a colored support or base. Such large-sized grains run short of the covering power of developed silver. The group of coexisting small-sized grains deviates from a sensitive region and not only contributes nothing to any optical density but makes the optical density lower because of the shortages of light-receiving quantity and sensitizing effect.

It is, therefore, usual that an amount of silver coated is increased and the both sides of a support are coated with.

Medical diagnoses require an X-ray light-sensitive material having the characteristic curve suitable for expressing the soft tissues such as the stomach and intestines or the bone tissues such as those of the hand and legs.

It is, however, not only difficult to satisfactorily express both soft and hard tones, but also lower in the efficiency of silver halide application, when using a single emulsion.

In some practical X-ray photographing examples prepared with conventional type direct radiographic light-sensitive materials, there have been some instances where even the following serious defects or inconveniences are found. To be more concrete, one of the most popular in-vivo organism sites subject to X-ray photographing is the chest. When reading chest X-ray photographs, the important sites are the blood vessels of the lung fields and the coronaries behind the heart.

Such lung fields are in a moderate density region (having a density of D=1.3 to 1.5). For reading the images of the blood vessels in the lung field, a relatively higher sharpness is required. At the same time, for reading the images of the coronaries, a wide latitude is required, because such coronary images are in a relatively lower density region (having a density of D=0.05 to 0.3).

With conventional high-gamma types of X-ray light-sensitive materials, the sharpness of a lung field image may be expressed high, while the image density of the coronary arteries may be expressed extremely low. Therefore, those light-sensitive materials have been practically unable to contribute to diagnoses. On the contrary, when using a low-gamma type X-ray light-sensitive material, the image of the coronary arteries has been able to express well, while a lung field image has been low in sharpness.

As the methods of forming an X-ray image capable of satisfying the above-mentioned two contradictory requirements, sensitivity-compensation type intensifying screens were studied and they are disclosed in, for example, Japanese Patent Publication Open to Public Inspection (hereinafter referred to as Japanese Patent O.P.I. Publication) Nos. 62-138800(1987), 62-170900(1987), 62-222200(1987), 62-231199(1987), 62-231200(1987), 62-238500(1987), 63-186200(1988), 63-223600(1988), 63-233340(1988) and 63-233399(1988).

However, these methods have been unable to compensate the differences between individuals and still not satisfactory to form an image suitable for efficient diagnoses.

On the other hand, the studies have been progressed from the aspect of controlling an X-ray dose. From these studies, an X-ray masking method or a scanning method using an X-ray pencil-beam spot was proposed and, further, a method using a scanning X-ray fan-beam by which the defects of X-ray pencil beams are improved was proposed. (Refer to U.S. Pat. No. 4,433,430.) However, in the X-ray photography using such a scanning fan-beam, the fan-beam fluxes have each the same intensity in the transverse direction when they cross through each of the thick, thin, hard and soft tissue sites of a subject, so that the details of an image in the transverse direction could not satisfactorily be expressed. For improving the above-mentioned problem, Japanese Patent O.P.I. Publication No. 62-129034(1987) proposed a divergent X-ray radiographic system (hereinafter referred to as an X-ray fan-flux regression scanning system) such as a scanning X-ray fan-beam flux system in which the fan-beam flux is diversified into a plurality of fan-beam fluxes and each individual flux is modulated separately by a feed-back system.

The above-mentioned X-ray photography using the X-ray fan-flux regression scanning system is very valuable, because it is capable of solving the differences between individual subjects and the obstacles of transversely positioned hard and soft tissues with the use of a simple X-ray film screen cassette so as to form excellent images if using an X-ray film having a gamma of not lower than 3. However, this method is still not satisfactory to express soft tissues coronary arteries covered by such soft tissues as. It has not, therefore, been achieved yet to provide any delicate and accurate diagnosis information.

SUMMARY OF THE INVENTION

One of the object of the invention is to provide an X-ray radiographic system capable of expressing a covered in-vivo organism and giving images having an excellent sharpness.

Another object of the invention is to provide an X-ray radiographic system without being affected by any differences among individual subjects or any unintentional movements of subjects.

The above-mentioned objects of the invention can be achieved with an X-ray radiographic system characterized in using a silver halide light-sensitive material comprising a support provided thereon with at least one emulsion layer having a covering power of not less than 45, for making an X-ray photography in which a scanning X-ray fan-beam flux is appropriately modulated by means of regulators provided to every plurally divided fan opening angle positions so as to move the regulators according to the scanning movements of the X-ray fan-beam.

BRIEF DESCRIPTION OF THE DRAWINGS

FIGS. 1(a) and 1(b) are the schematic plane and side views respectively of an X-ray fan flux regression scanner relating to the invention.

DETAILED DESCRIPTION OF THE INVENTION

Figure 2:
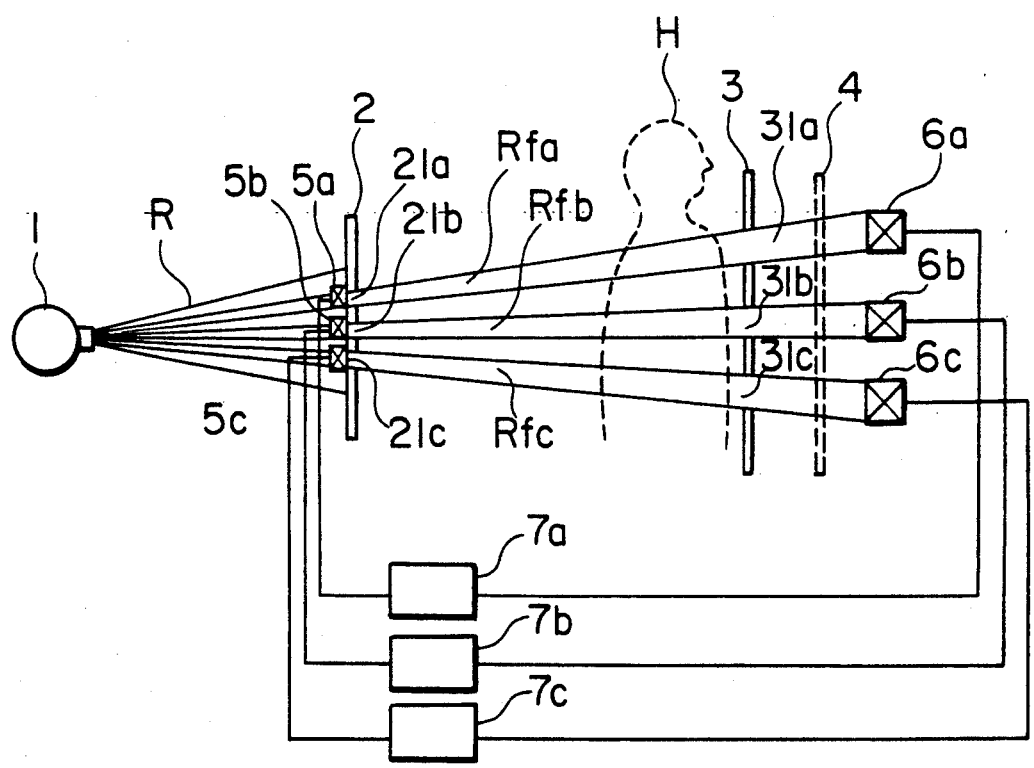
FIG. 2 is the schematic side view of a triple-unit system scanner.

The X-ray photography in the X-ray radiographic system of the invention is based on the above-described X-ray fan flux regression scanning operation and the following examples relating to the invention will be detailed with reference to the drawings given below.

FIG. 1(a) is a schematic plane view of the above-mentioned regression scanning mechanism, and FIG. 1(b) is a schematic side view thereof.

In the above figures, reference numeral 1 indicates an X-ray source, R is a conical X-ray beam flux, 2 is a collimeter comprising a material capable of shielding X-rays and provided with slot 21 capable of changing the conical X-ray beam into a fan-shaped flux, Rf is a fan-shaped X-ray beam flux, and H is a subject.

Numeral 3 is a collimeter capable of shielding scattering X-rays emitted from subject H and provided with slot 31 having a size coordinated with fan flux Rf formed by slot 21, and 4 is an X-ray film relating to the invention.

Numeral 5 is an X-ray flux regulator alley which divides the opening of the fan flux into specific plural opening angle sections and comprises regulators 5i (of which i=1,2, ..., n) provided correspondingly to the sections. Each regulator 5i may be of the shutter system, the wedge type or the multistage type filter system capable of controlling an X-ray transmission quantity.

Numeral 6 is a sensor alley comprising X-ray flux sensors 6i (of which i=1,2, ... ,n) so provided as to make both of sensors 6i and 5i to be in the same direction and size.

Collimeters 2 and 3 and regulator alleys 5 and 6 each move synchronously with scanning movements while keeping them all consistency, and an X-ray dose information sent from sensors 6i is directly or stored once in a memory device and is then transmitted by feed-back device 7 to regulators 5i so as to urge the control of regulator 5i to be consistent with each site of a subject and to give an optimum X-ray dose to every site to meet the characteristics of an X-ray film.

For saving an X-ray source operation time and preventing a subject from blur, it is also permitted that the X-ray fan flux regression scanning system may be so arranged as a complex scanning system to which plural units of a series of slot 21-regulator alley 5-slot 31-sensor alley 6 are provided. FIG. 2 illustrates a triple-unit system as an example of the embodiments thereof.

In silver halide light-sensitive materials relating to the invention, the covering power thereof is not less than 45 and, preferably, within the range of 50 to 200. If it is not less than 200, the emulsion preparation techniques are affected by a sensitivity hinderance.

The term, 'covering power' used in the invention means a value obtained by dividing a maximum optical density of a silver image produced by exposing a light-sensitive material to light and processing it by an amount of developed silver in terms of g/dm$^2$ at the point of the above-mentioned maximum optical density. In the invention, the processing requirements for determining a covering power are as follows: Processing requirements Using the following Developer-1 and according to the following processing steps, a light-sensitive material is processed with a roller-transport type automatic processor.

| | Processing temperature | Processing time |
|---|---|---|
| Developing | 35° C. | 30 sec. |
| Fixing | 34° C. | 20 sec. |
| Washing | 33° C. | 18 sec. |
| Drying | 45° C. | 22 sec. |
| Developer-1 | | |
| Potassium sulfite | | 55.0 g |
| Hydroquinone | | 25.0 g |
| 1-phenyl-3-pyrazolidone | | 1.2 g |
| Boric acid | | 10.0 g |
| Potassium hydroxide | | 21.0 g |
| Triethylene glycol | | 17.5 g |
| 5-methylbenztriazole | | 0.04 g |
| 5-nitrobenzimidazole | | 0.11 g |
| 1-phenyl-5-mercaptotetrazole | | 0.015 g |
| Glutalaldehyde bisulfite | | 15.0 g |
| Glacial acetic acid | | 16.0 g |
| Potassium bromide | | 4.0 g |
| Add water to make | | 1 liter |

There is no special limitation to the fixers, provided, they are acidic hardening fixers including, for example, Konica New XF manufactured by Konica Corporation.

In the preferable embodiments of the invention, at least one kind of monodisperse type emulsion is used. When using such a monodisperse type emulsion, a desirable emulsion grain-size distribution can be obtained.

In the invention, the term, 'monodisperse type emulsion', means those satisfying the following expression:

$$\frac{S}{\bar{r}} < 0.20$$

and, the term, 'polydisperse type emulsion', means those satisfying the following expression:

$$\frac{S}{\bar{r}} \geq 0.20$$

wherein $\bar{r}$ represents an average grain-size by number and S represents a standard deviation.

A grain-size may be obtained either in the manner that, using an electron microscopic photograph of silver halide grains, the projective area of the grain is converted into the circular area thereof, therefrom obtaining the diameter of the circular area, or in the other manner that a stokes-diameter is measured in a centrifugal sedimentation liquid phase method. A grain-size distribution may be obtained similarly from such an electron microscopic photograph.

The X-ray light-sensitive materials of the invention also include, preferably, those containing an emulsion comprising two or more kinds of monodisperse type emulsions each having the different average grain-sizes.

When embodying the invention, any one of silver chloride, silver bromide, silver chlorobromide, silver iodobromide, silver chloroiodobromide and so on may be used as a silver halide. Among them, the preferable ones include a silver iodobromide, and the most preferable one is silver iodobromide comprising grains having the portions wherein silver iodide is unevenly distributed.

From the viewpoint of the above-mentioned covering power, it is advantageous to use silver halide grains not substantially containing silver iodide on the surface thereof. The average grain-size thereof is within the range of 0.1 to 4 μm and, preferably, 0.2 to 3 μm.

Silver should preferably be used in an amount of 0.6 to 1.6 g per g of gelatin and, in other words, in the following silver/gelatin ratio: Ag(g)/Gel(g)=0.6 to 1.6.

Silver is to be coated in an amount of not more than 4.0 g/m² in terms of silver content per one side of a support and, preferably, 1.5 to 3.5 g/m².

For a monodisperse type emulsion, it is preferred to use a silver iodobromide emulsion having the portions wherein silver iodide is unevenly distributed in an amount of not less than 10 mol % each inside the silver iodobromide emulsion grains. When this is the case, the effects of the invention can satisfactorily be achieved without increasing pressure fog any more. It is also preferable that silver iodide is unevenly distributed in an amount of not less than 30 mol % inside the silver iodobromide emulsion grains. It is further preferable that the whole silver iodide content should be within the range of 0.1 to 10 mol %.

It is also preferable to use an embodiment containing a monodisperse type emulsion having a silver bromide shell structure in which the outside of the shell is covered with silver bromide. In this case, it is preferable that the silver bromide shell thickness is within the range of 0.10 to 1.00 μm and within the range of 20 to 65% of the grain diameter. It is further preferable that the shell thickness is within the range of 0.30 to 0.85 μm and within the range of 40 to 60% of the grain diameter. In the case where an emulsion has the whole silver iodide content of 2 mol % and a portion containing unevenly distributed silver iodide in an amount of 10 to 30 mol % each inside the grains, it is preferable that the above-mentioned shell thickness should be within the range of 0.10 to 1.00 μm and within the range of 40 to 60% of the grain diameter, though the most preferable values may be varied depending upon the grain-sizes.

Any methods of preparing a monodisperse type silver iodobromide emulsion having the portions locally containing highly concentrated silver iodide are applicable to the invention regardless of either using seed crystals or not. However, it is preferable to use seed crystals.

When not using any seed crystal, nuclei are grown by supplying halide ions containing silver ions and halide ions containing highly concentrated iodine ions in an amount of at least 20 mol %, because a mother liquid containing protective gelatin does not contain any silver halides such as those capable of forming grown nuclei before commencing a ripening process. And, keeping the supply of the halide ions, the grains are then grown from the grown nuclei. Finally, shell layers are formed with silver halides not containing any silver iodide.

When using seed crystals, silver iodide of at least 10 mol % is formed only on each seed crystal, and the seed crystals may then be covered with the shell layers. Or, it is also permitted that a silver iodide contents of the seed crystals are reduced in advance and silver iodide of at least 10 mol % is formed in the seed crystal growing process, and the seed crystals may then be covered with the shell layers.

In these instances, the seed crystal sizes and grain-size distribution obtained each in the former method become greater than those in the latter method because the silver iodide contents of the total grains are preferably within the range of 0.1 to 10 mol % to the total silver halides in the invention. In the embodiments of the invention, a multi-layered structure such as those prepared in the latter method is preferable.

When embodying the invention, it is preferable to keep the pAg of the mother liquid containing protective colloid should be not lower than 10.5 in the course of growing the grains before the grains are chemically sensitized. In particular, it is more preferable to make the grains round by passing them at least once through an extremely excessive bromine ion atmosphere such as at not lower than pAg 11.5.

When using an emulsion consisting only of a monodisperse type emulsion, a high-gamma light-sensitive material may be obtained.

It is permitted that the light-sensitive layers comprising silver halide grains of the invention may be either of the single-layered type or of the two or more multi-layered type, provided, the one- or two-layered type is preferable.

Such silver halide emulsion layers may be provided to either the both sides of a base or one side thereof. When providing them to the both sides of the base, the grain-size distributions thereof and photographic specification thereof may be either the same with or the different from each other.

It is also preferable to protect the emulsion layers upon forming protective layers. It is further permitted to provide the emulsion layers thereon or thereunder with interlayers or filter layers including, for example, colored non-light-sensitive layers.

The crystal habits of the silver halides may be either of a regular or twin crystal, and the appearances thereof may be in the mixture of variously crystallized grains such as tabular or globular grains, such as a cube, tetradecahedron, octahedron or the like, according to the growing conditions of crystal faces.

For example, these crystals may also be aggregated silver halide crystals including that aggregated an oxide crystal such as a PbO crystal with a silver halide crystal such as a silver chloride crystal; an epitaxially grown silver halide crystals including those in which silver chloride, silver iodobromide or silver iodide is epitaxially grown on silver chloride; or crystals in which a normal hexahedral silver chloride is oriently overlapped a hexahedral or normal octahedral silver iodide.

It is further permitted to use an emulsion of which not less than 50% of the total projective area is occupied by ultra-thin tabular-shaped silver halide grains having a grain-size not less than five times as large as the thickness thereof.

For the details thereof, refer to Japanese Patent O.P.I. Publication Nos. 58-127921(1983) and 58-113927(1983).

It is also permitted to use internal latent image forming type silver halide grains and surface latent image forming type silver halide grains together in combination, as described in for example, Japanese Patent Examined Publication No. 41-2086(1966).

In the embodiments of the invention, silver halide grains applicable to the silver halide emulsions can be prepared in the methods well-known in the field of the photographic art, such as a neutral method, an acidic method, an ammoniacal method, a normal precipitation method, a reverse precipitation method, a double-jet precipitation method, a controlled-double-jet precipitation method, a conversion method, and a core/shell method.

As another type of the double-jet precipitation methods, a triple-jet precipitation method may also be used, in which soluble halides having each different compositions, to a soluble silver salt, such as a soluble bromide and solvent for silver halide are added independently.

It is also permitted to use a method for forming grains in an excessive silver ion atmosphere, that is, the so-called reverse precipitation method.

As one of the double-jet precipitation methods, the so-called controlled-double-jet precipitation method, that is a method of keeping a pAg value constant in a liquid phase in which silver halides may be produced.

It is further permitted to use separately prepared two or more kinds of silver halide emulsions in combination.

The above-described silver halide grains or silver halide emulsions should preferably contain at least one kind of the soluble salts of metals selected from the group consisting of those of iridium, thallium, palladium, rhodium, zinc, nickel, cobalt, uranium, thorium, strontium, tangsten and platinum. It is more preferable to contain at least one kind of the salts of thallium, palladium or iridium. The content thereof is within the range of preferably $10^{-6}$ to $10^{-1}$ mols per mol of Ag. These salts may be used independently or in combination. They may be added at any time and to any positions. When they are added, it may be expected to improve flash-exposure characteristics, prevent a pressure desensitization and latent image regression, and display the effects of sensitization and so forth.

The X-ray light-sensitive materials of the invention may be sensitized in various sensitizing means such as a dye-sensitization, or a chemical-sensitization.

For example, when using a mixture of emulsions each containing silver halide grains having severally different average grain-sizes, a chemical sensitization optimum for those grains may be applied, thereby achieving a further higher sensitization. The applicable chemical sensitizations include, for example, a reduction sensitization, a noble metal sensitization, a sulfur sensitization, and a selenium sensitization. These sensitizations may be applied independently or in combination.

It is desired to carry out the reduction sensitization while ripening the silver halide grains in a relatively lower pAg atmosphere by making use of a tin chloride or an organic reducing agent. It is also permitted to carry out the reduction sensitization inside the grains.

The noble metal sensitization may be carried out with a gold salt, a platinum salt, or a palladium salt.

The sulfur sensitization may be carried out with hypo, or thioether.

The selenium sensitization should preferably be carried out with, for example, selenathiourea.

Besides the above, if required, the sensitization may be optically carried out to any desired wavelength region by using, independently or in combination, an optical sensitizer such as cyanine dyes and merocyanine dyes.

It is permitted to use the dyes described in, for example, U.S. Pat. Nos. 2,493,784, 2,519,001, 2,977,229, 3,480,343, 3,672,897, 3,703,377, 2,688,545, 2,912,329, 3,397,060, 3,511,664, 3,522,052, 3,527,641, 3,615,613, 3,615,832, 3,615,635, 3,615,641, 3,617,295, 3,617,293, 3,628,964, 3,835,721, 3,656,959, 3,694,217, 3,743,510, 3,769,301 and 3,793,020.

When preparing a silver halide emulsion to embody the invention, it is allowed to use gelatin, a gelatin derivative and a synthesized hydrophilic polymer as a protective colloid and, further, various types of photographic additives may be contained in the emulsion.

Various kinds of additives which have usually been used may be added into the silver halide emulsions relating to the invention. To be more concrete, stabilizers and antifoggants which are popularly used may be added therein. The particularly preferable compounds for the purpose include, for example, 4-hydroxy-6-methyl-1,3,3a,7-tetrazaindene, 5,6-trimethylene-7-hydroxy-S-triazolo(1,5-a)pyrimidine, 5-methyl-7-hydroxy-S-triazolo(1,5-a)pyrimidine, gallates, mercaptans, benztriazoles, and benzimidazoles.

The silver halide emulsions relating to the invention may be used in the coating solution thereof with a hardener for photographic use including, for example, those of the aldehyde type, aziridine type, isooxazole type, epoxy type, vinylsulfone type, acrylonitrile type, carbodiimide type and, besides, a maleimide type, acetylene type, methanesulfonic acid ester type, triazine type and polymer type.

Further, a thickener, a gelatin plasticizer, a latex, and a matting agent may also be used together.

In coating the component layers of X-ray light-sensitive materials relating to the invention, a coating assistant such as a saponin or sulfosuccinic acid type surfactant or an anionic surfactant may be used.

In an X-ray light-sensitive material relating to the invention, it is permitted to use a dye in the layer which is below the emulsion layer thereof and adjacent to the support thereof so that the so-called cross-over effect may be reduced and, further, the dye may be added to a protective layer and/or the emulsion layers so as to improve the sharpness of an image or to reduce fogs produced by a safelight.

Any coating methods having usually been used may be used, such as a dipping method, a slide-hopper method, an extruder method or a curtain-coating method.

Emulsions may be coated on the both sides or one side of a support and, when coating the emulsion on the both sides of the support, the emulsion may be coated in a symmetric or asymmetric arrangement on the support.

In the case of an X-ray light-sensitive material which is to be coated on the both sides thereof with an emulsion, the so-called print-through or cross-over effects may be reduced by coating a relatively lower sensitive emulsion in contact with a support and a relatively higher sensitive emulsion thereon.

In the case of applying the invention to an medical X-ray photography, an exposure is made by using a fluorescent intensifying screen principally comprising a fluorescent substance from which near-UV or visible rays are emitted when the screen is exposed to X-rays, and by closely contacting the screen with the both sides of an X-ray light-sensitive material.

Such fluorescent intensifying screen mentioned herein is, for example, that containing a fluorescent ray emitting component principally comprising calcium tangstate $CaWO_4$, or that containing a fluorescent ray emitting component principally comprising a rare-earth compound activated with terbium.

The X-ray light-sensitive materials of the invention can be developed in various processes. As a black-and-white developers, any ordinarily applicable developers may be used, such as hydroquinone, 1-phenyl-3-pyrazolidone, N-methyl-p-aminophenol and p-phenylenediamine. They may be used independently or in combination. As the other additives, any popular ones may be used.

The developer containing an aldehyde type hardener may also be applied to the silver halide light-sensitive materials relating to the invention. These developers include, for example, the developers which are corresponded to photographic fields and contain dialdehydes such as maleic dialdehyde or glutaraldehyde and the sodium bisulfite thereof. On the other hand, as the fixers, those containing a thiosulfate, a water-soluble aluminium compound, acetic acid or a dibasic acid such as citric acid, tartaric acid and the salts thereof may be used. As the other additives for them, the popularly useful ones may be used.

For further details, Research Disclosure No. 17643, Vol. 176, pp. 25-30, and L. F. A. Mason, 'Photographic Processing Chemistry', 1975, London, Focal Press, may be referred to.

The processing temperatures may be normally selected from between 18° C. and 50° C., however, it will do to select from a temperature lower than 18° C. or higher than 50° C. The total processing time is selected from between 20 seconds and 10 seconds.

EXAMPLES

The invention will be detailed with reference to the following examples.

EXAMPLE 1

(1) Preparation of emulsions

A) Preparation of seed crystal grains

First of all, the following Solutions A through E were prepared.

| Solution A: | $H_2O$ | 23 l |
| --- | --- | --- |
| | KBr | 4.1 g |
| | Gelatin | 0.2 Kg |
| Solution B: | $H_2O$ | 5.2 l |
| | KBr | 130 g |
| | KI | 3.6 g |
| | Gelatin | 110 g |
| | $H_2SO_4$ (Diluted) | 77.0 m |
| Solution C: | $H_2O$ | 6.0 l |
| | KBr | 1.90 Kg |
| | KI | 54 g |
| | Gelatin | 150 g |
| Solution D: | $H_2O$ | 5.4 l |
| | $AgNO_3$ | 190 g |
| Solution E: | $H_2O$ | 6.4 l |
| | $AgNO_3$ | 2.82 Kg |

Solution A was added into a reaction vessel and was then kept at 60° C. The other solutions were added at 59° C. When adding them, Solutions B and D were added in a controlled double-jet precipitation method by taking 30 minutes, and Solutions C and E in the same method by taking 105 minutes, respectively. They were all stirred at 800 rpm. The flow rate was accelerated in proportion to the increase in the total surface area of silver halide grains which were being grown. When flowing the solutions in, the solutions were added at a flow rate so as not to produce any newly growing neclei, not to bring about the phenomenon so-called Oswald ripening and also not to spread the grain-size distribution.

In adding each of a silver ion solution and a halide ion solution, the pAg values thereof were adjusted with a potassium bromide solution so as to be $8.3\pm0.05$ and the pH values, with acetic acid, to be $pH=2.0\pm0.1$, respectively. The resulting emulsion contained AgI in an amount of 2 mol % and had a grain-size of 0.30 μm and $\sigma/r=0.11$. The (111) planes thereof were of 5% and the others were (100) planes. The resulting emulsion was a monodisperse type emulsion having cubic tetradecahedral grains whose tops and edges were slightly rounded.

After the growth of the seed crystals, the pH of the emulsion was adjusted to be pH $6.00\pm0.3$ with a sodium carbonate solution and the temperature thereof was then lowered to be 40° C. The emulsion was further desalted in a flocculation precipitation method with both of an aqueous solution of naphthalenesulfonic acid formalin resin and a solution of magnesium sulfate and, further, gelatin and phenol were added thereto, so that 16.9 kg of a seed crystal emulsion having a pAg of 8.50 and pH of 5.85 was obtained.

B) Preparation of monodisperse type grains

An example of a covering layer, that is a shell, will be given below, provided that the covering layer was prepared by using seed crystals whose grain-sizes were grown up from 0.3 μm to finally 0.87 μm.

First of all, the following solutions were prepared.

| Solution J: | $H_2O$ | 13 l |
| --- | --- | --- |
| | Gelatin | 110 Kg |
| | Conc. aqueous ammonia | 1.5 l |
| | Glacial acetic acid | 0.12 l |
| Solution K: | $H_2O$ | 2.34 l |
| | KBr | 214 g |
| | KI | 130 g |
| | Gelatin | 12 g |
| Solution L: | $H_2O$ | 1.54 l |
| | KBr | 2.86 Kg |
| | Gelatin | 150 g |
| Solution M: | $H_2O$ | 1.25 l |
| | $AgNO_3$ | 280 g |
| | Conc. aqueous ammonia | 230 ml |
| Solution N: | $H_2O$ | 1.95 l |
| | $AgNO_3$ | 435 g |
| | Conc. aqueous ammonia | 360 ml |
| Solution O: | $H_2O$ | 1.70 l |
| | $AgNO_3$ | 3.70 Kg |
| | Conc. aqueous ammonia | 300 ml |
| | Add water to make | 6.85 l |
| Solution P: | $H_2O$ | 3.9 l |
| | KBr | 2.25 Kg |

Solution J was added while keeping the temperature at 45° C. and an agitation was made with an agitator at 800 rpm.

The pH of Solution J was adjusted by adding acetic acid to be 9.90. Taking 1.039 Kg of seed grains, they were dispersed in Solution J so as to be suspended therein. After Solution M was added thereto at a constant rate by taking 5 minutes, Solutions K and N were added at the same time by taking 45 minutes. The pAg value at this time was 8.08.

The pH and pAg thereof were adjusted to be 8.83 and 8.89, respectively, by taking 20 minutes with both of a KBr solution and acetic acid, and then Solutions O and L were added at the same time by taking 30 minutes. At this time, the ratio of the flow rate at the time when starting the addition to the flow rate at the time when completing the addition was 1:10, and the flow rates were accelerated with the passage of the adding time. Also, the pH was lowered from 8.83 down to 8.00 in proportion to the changes of the flowed amounts.

Further, Solution P was rush-added when Solutions O and L were added in the amount of two third as much as the total amount.

At this time, the pAg and pH were raised up from 8.89 to and 11.1. After adding acetic acid to make pH to be 6.0, a desalting treatment was made in the same way as in the seed grains, and gelatin was added, so that an emulsion having a pH of 5.90 and a pAg of 8.72 was obtained. The resulting emulsion was a monodisperse type tetradecahedral silver iodobromide emulsion having an AgI content of 3 mol %, a grain-size distribution of $\sigma/r=0.16$, (111) planes of 20% and (100) planes of 80%. (Hereinafter referred to as Emulsion E-1.)

In the same manner as in E-1, the monodisperse type silver iodobromide emulsions E-2 having a grain-size of 1.20 μm by taking seed grains in an amount of 0.395 Kg, and E-3 having a grain-size of 0.50 μm by taking seed grains in an amount of 5.47 Kg were obtained, respectively.

C) Preparation of globular block-shaped grains

| Solution 1: | $H_2O$ | 17 l |
| | KI | 126 g |
| | Gelatin | 210 g |
| Solution 2: | $H_2O$ | 14 l |
| | KBr | 3.5 Kg |
| | Glacial acetic acid | 0.32 l |
| Solution 3: | $H_2O$ | 9.45 l |
| | $AgNO_3$ | 4.2 Kg |
| | $NH_4OH$ | |
| | (Conc. aqueous ammonia) | 3.3 l |
| Solution 4: | Na $IrCl_6$ | 1.0 mg |
| | $H_2O$ | 100 ml |

While keeping Solution 1 at 57° C. and stirring it at 800 rpm, a 3% amount of Solution 3 was added into Solution 1 at a constant rate by taking one minute. After allowing to stand for one minute, Solution 2 and the remaining Solution 3 were started to add therein at the same time, provided, Solution 2 was added by taking 10 minutes and Solution 3 by taking 20 minutes at a constant rate, respectively. One minute after adding Solution 3, Solution 4 was rush-added. Then, after a 3-minute ripening, acetic acid was added so as to adjust the pH to be 6.00. While adding Solutions 2 and 3, the pAg was changed from 11 to 10.5.

Further, a desalting treatment was made in the same manner as in E-1 and gelatin was added, so that 14.5 Kg of an emulsion having a pH of 5.90 and a pAg of 8.71 was obtained. (Hereinafter referred to as E-4). The resulting emulsion was proved to be a twin-crystal emulsion having an average grain-size r of 1.20 μm, a grain-size dispersion of $\sigma/r=0.24$ and (111) planes of not less than 99%, when the emulsion was confirmed from the electron microscopic photo graph thereof.

D) Preparation of tabular-shaped grains

While stirring, at 800 rpm, an aqueous solution prepared by dissolving 6 g of potassium bromide and 30 g of gelatin into 3.7 l of distilled water, an aqueous 14% potassium bromide solution and an aqueous 20% silver nitrate solution were added thereinto in a controlled double-jet precipitation method at a fixed flow rate, at 55° C., for one minute, and at pBr=1.0.

(In this addition ①, 2.4% of the total silver amount was consumed.)

Next, 300 ml of an aqueous 17% gelatin solution was added and, with keeping it at 55° C. and stirring it at 800 rpm, an aqueous 20% silver nitrate solution was added at a fixed flow rate so as to make pBr to be 1.40. (In this addition ②, 5.0% of the total silver amount was consumed.)

Further, a 20% potassium bromide solution and an aqueous 33% silver nitrate solution were added in a controlled double-jet precipitation method by taking 80 minutes. (In this addition ③, 92.6% of the total silver amount was consumed.) In the course of the addition, the temperature and pBr were kept at 55° C. and 1.50, respectively. And, the amount of silver nitrate used in the emulsion was 425 g. The resulting emulsion was desalted in the same manner as in E-1 and gelatin was added, so that Emulsion E-5 was obtained. In the emulsion, the ratio of the average grain-size to the grain thickness was 8.2 and the average grain-size was $\bar{r}=0.9$ μm.

Emulsion E-6 was prepared so as to make a ratio of the average grain-size to the grain thickness to be 6.3 and to have the average grain-size of $\bar{r}=0.8$ μm in the same preparation procedures as in the above-described Emulsion E-5, except that a solution containing 8.3 g of potassium iodide was added by interrupting the additions of the potassium bromide solution and the silver nitrate solution, at the point of time when 57% of the total silver amount was consumed in the course of Addition ③.

Emulsions E-1 through E-6 were added by sodium thiocyanate, aurochloric acid and hypo. The resulting emulsions were chemically ripened to satisfy the conditions for obtaining the respective optimum sensitivities and were then added by a gelatin solution containing 4-hydroxy-6-methyl-1,3,3a,7-tetrazaindene in an amount of $2\times10^{-2}$ mols per mol of silver halides used. The pH of each emulsion was adjusted to be 6.00 and they were set by cooling down, and stored.

(2) Preparations of test samples

Samples were prepared in the following manner:

The silver halide emulsions each prepared in the manner described in the foregoing article (1) were mixed in the combination shown in Table-1 and the following additives were added in the following amounts per mol of silver halides used.

| t-butyl-catechol | 400 mg |
| polyvinyl pyrolidone | 1.0 g |
| (molecular weight: 10,000) | |
| styrene-maleic anhydride copolymer | 2.5 g |
| polyethylene acrylate | 2.5 g |
| (molecular weight: 250,000) | |
| trimethylol propane | 10 g |
| diethylene glycol | 5 g |
| nitrophenyl-triphenylphosphonium chloride | 50 mg |
| ammonium 1,3-dihydroxybenzene-4-sulfonate | 4 g |
| sodium 2-mercaptobenzimidazole-5-sulfonate | 15 mg |
| 2-mercaptobenzthiazole | 10 mg |

[benzothiazolium structure with $CH_3SO_3^\ominus$ counterion] — 70 mg $C_4H_9OCH_2CHCH_2N\begin{matrix}CH_2COOH\\ \\CH_2COOH\end{matrix}$  with OH on middle carbon — 1 g 1,1-dimethylol-1-bromo-1-nitromethane — 70 mg

[triphenyl formazan-type structure] — 150 mg

Further, as the additives for protective layers, the following compounds were added in the following amounts per g of gelatin used.

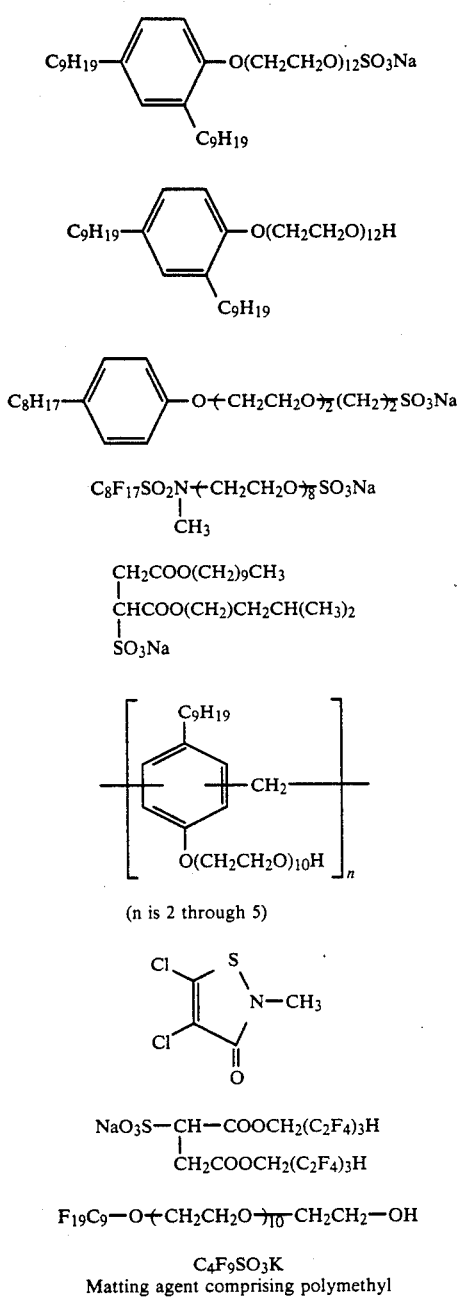

| | 12 mg |
| | 2 mg |
| | 4 mg |
| | 6 mg |
| | 7 mg |
| | 15 mg |
| | 10 mg |
| | 5 mg |
| | 3 mg |
| $C_4F_9SO_3K$ | 2 mg |
| Matting agent comprising polymethyl methacrylate having an average particle-size of 7 μm | 7 mg |
| colloidal silica having an average particle-size of 0.013 μm | 70 mg |
| formaldehyde | 9 mg |
| glyoxal | 6 mg |
| sodium 2-hydroxy-4,6-dichloro-1,3,5-triazine | 4 mg |

As the protective layers, an aqueous gelatin solution containing the above-given additives was simultaneously coated, at a coating speed of 150 m/min., on the both surfaces of support A prepared by following the support preparation procedures described in the example-(1) of Japanese Patent Application No. 62-186,436(1987), and the coated protective layers were dried by taking 2.5 minutes, so that the samples were obtained. In the samples, the total amount of silver coated on both surfaces was 6.5 g/m², the total amount of gelatin coated on both surfaces of the protective layer was 2.6 g/m², and the total amount of gelatin coated on both surfaces of the emulsion layer was 4.8 g/m².

(3) Testing method

After the samples were coated and then stored for 7 days at 25° C. and 50% RH, they were sandwiched between X-ray intensifying screens NR-100 manufactured by Konica Corp. Then, they were tested with an X-ray fan flux regression scanner shown in FIG. 2 under the conditions of a distance of 1.8 m, a tube voltage of 125 KVp, a tube current of 350 mA and a total scanning of time of 1 second.

Next, the samples were processed with an automatic processor KX-500 manufactured by Konica Corp. so as to meet the requirements for obtaining a satisfactory covering power.

The fixer used therein had the following compositions:

| | |
|---|---|
| ammonium thiosulfate | 180.0 g |
| sodium thiosulfate.pentahydride | 45.0 g |
| sodium sulfite anhydride | 20.0 g |
| boric acid | 8.0 g |
| disodium ethylenediaminetetraacetate | 0.1 g |
| ammonium sulfate | 15.0 g |
| aluminium sulfate, decahydride | 5.0 g |
| sulfuric acid | 2.0 g |
| tartaric acid | 3.5 g |
| glacial acetic acid | 22.0 g |
| add water to make | 1 liter |
| adjust pH to be | 4.2 |

On each of the processed samples, the images of the coronaries covered by the heart were observed.

The results thereof are shown in Table-1.

TABLE 1

| Sample No. | Emulsion & mixing rate | Covering power | Coronary images | Remark |
|---|---|---|---|---|
| 1 | E-4 | 40 | Details not clear | Comparison |
| 2 | E-1:E-2:E-3 = 2:7:1 | 42 | " | " |
| 3 | = 4:2:4 | 59 | Details clear & sharp | Invention |
| 4 | = 4:1:5 | 64 | " | " |
| 5 | = 3:2:5 | 63 | " | " |
| 6 | = 6:0.5:3.5 | 59 | " | " |
| 7 | E-5 | 64 | " | " |
| 8 | E-6 | 62 | " | " |

For the comparison, a sample was x-rayed through a chest-site sensitivity compensation type intensifying screen CS-III manufactured by Kasei Optonics Co. in an ordinary direct X-ray system. The results were found to be quite unsharp in the coronary images covered by the heart as compared to the results from the inventive samples.

EXAMPLE 2

When carrying out a chemical sensitization in the course of preparing an emulsion, the following sensitizing dyes and potassium iodide were so used as to have an absorption peak in a green spectral region. The X-ray intensifying screen was replaced by that of KO-125 manufactured by Konica Corp.

Silver was coated on the both sides in an amount of 4.0 g/m².

Thereby, a 45-second processing was tried in the X-raying conditions of a tube current of 280 mA and by using an automatic processor SRX-501 manufactured by Konica Corp. and a processing solutions XD-SR and XF-SR each manufactured also by Konica Corp. The results thereof were the same as in Example 1.

Sensitizing dyes

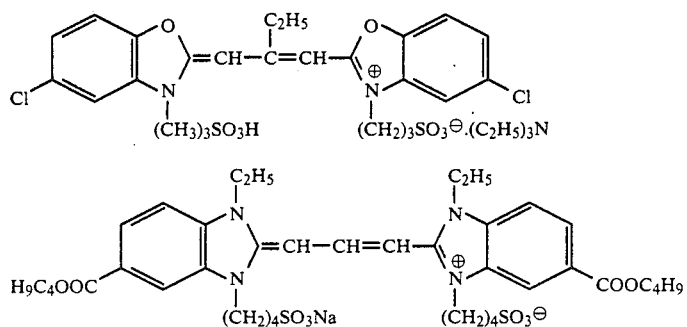

What is claimed is:

1. An X-ray radiography system comprising an exposure apparatus having;
   (1) an X-ray radiating means
   (2) a collimator for generating a fan-beam
   (3) a regulator movable along the fan-beam scanning direction and for dividing the fan-beam into a plurality of angle section and controlling penetrating power, and
   (4) a silver halide photosensitive material comprising at least one emulsion layer having a covering power of not less than 45.

2. The X-ray radiography system of claim 1, wherein said emulsion layer has a covering power of 50 to 200.

3. The X-ray radiography system of claim 1, wherein said emulsion layer comprises silver halide grains having a silver iodine content of 0.1 to 10 mol %.

4. The X-ray radiography system of claim 3, wherein said silver halide grains are silver iodobromide grains wherein silver iodine distribution is uneven.

5. The X-ray radiography system of claim 4, wherein an average diameter of said silver halide grains is 0.1 μm to 4 μm.

6. The X-ray radiography system of claim 4, wherein an average diameter of said silver halide grains is of 0.2 μm to 3 μm.

7. The X-ray radiography system of claim 4, wherein said silver iodobromide grain comprises a portion wherein silver iodine concentration is more than 10 mol %.

8. The X-ray radiography system of claim 4, wherein said silver ioidobromide grain comprises a portion wherein silver iodine concentration is more than 30 mol %.

9. The X-ray radiography system of claim 4, wherein said silver iodobromide grain comprises a silver bromide shell having a thickness of 0.10 to 1.00 μm.

10. The X-ray radiography system of claim 1, wherein said silver halide photosensitive material has a silver content of 0.6 g to 1.6 g per 1 g of gelatin.

11. The X-ray radiography system of claim 1, wherein said silver halide photosensitive material has a silver content of 1.5 to 3.5 g on square meter per one side.

* * * * *